United States Patent [19]

Welsh et al.

[11] Patent Number: 5,234,922

[45] Date of Patent: Aug. 10, 1993

[54] USE OF SULFONYLUREAS AND OTHER POTASSIUM CHANNEL REGULATORS TO TREAT SECRETORY DIARRHEA

[75] Inventors: Michael J. Welsh, Riverside; David N. Sheppard, Coralville, both of Iowa

[73] Assignee: University of Iowa Research Foundation, Oakdale, Iowa

[21] Appl. No.: 952,279

[22] Filed: Sep. 28, 1992

[51] Int. Cl.5 .............................................. A61K 31/54
[52] U.S. Cl. .............................. 514/223.2; 514/223.5; 514/275; 514/422; 514/593; 514/592
[58] Field of Search .................. 514/223.2, 223.5, 275, 514/422, 593, 592

[56] References Cited

U.S. PATENT DOCUMENTS 5,100,647  3/1992  Agus et al. ............................ 424/45

Primary Examiner—S. J. Friedman
Assistant Examiner—William Jarvis
Attorney, Agent, or Firm—Zarley, McKee, Thomte, Voorhees & Sease

[57] ABSTRACT

Methods for the treatment of secretory diarrhea comprised of administering to a patient in need thereof, an effective amount of a CFTR chloride channel blocker or a potassium channel opener are disclosed. The CFTR chloride channel blocker is a sulfonylurea of the group consisting of tolbutamide, glibenclamide, and related analogs. The potassium channel opener is selected from the group consisting of diazoxide, lemakalim, and minoxidil sulfate.

7 Claims, No Drawings

USE OF SULFONYLUREAS AND OTHER POTASSIUM CHANNEL REGULATORS TO TREAT SECRETORY DIARRHEA

BACKGROUND OF THE INVENTION

The present understanding of the underlying pathophysiological mechanism of acute secretory diarrhea is growing steadily. Secretory diarrhea can accompany gastrointestinal disorders such as inflammatory bowel disease. Acute diarrhea is a world-wide problem, and easily accounts for over a million deaths per year. Medical and pharmacological textbooks generally delineate two classifications for anti-diarrheal medications. The first group are known as astringents. The second group are opium derivatives. While such medications have met with some degree of success, it is an alarming fact that drug development specifically targeting diarrheal disease has been, until recently, almost nonexistent.

Probably the most significant event in the treatment of diarrheal disease in the past one hundred years has been the use of oral glucose-electrolyte solutions. But, there still is a need recognized by world-wide health organizations for continuing effort in diarrhea therapies.

Recent studies of electrolyte transport by intestinal mucosa have provided valuable information concerning the regulation of biochemical events involved in diarrhea. While there is still much refinement work needed, it has now become apparent that a method of treatment of diarrhea would be to control electrolyte transport, particularly chloride secretion.

In chloride secretion, chloride enters the cell across the basolateral membrane on a cotransporter that is coupled to entry of $Na^+$ and $K^+$. The entry step is electrically neutral because the charge on the anion is balanced by the charges on the cations. The cotransporter accumulates $Cl^-$ in the cell at a value greater than that predicted for electro-chemical equilibrium. Removal of $Na^+$ from the submucosal solution or addition of a loop diuretic (furosemide or bumetanide) inhibits $Cl^-$ accumulation in the cell, thereby inhibiting $Cl^-$ secretion. Na-K-ATPase in the basolateral membrane maintains the $Na^+$ concentration within the cell lower than that in the submucosal solution; that gradient across the basolateral membrane provides the energy required to pull $Cl^-$ and $K^+$ into the cell. As the pump hydrolyzes ATP, it drives $Na^+$ out of the cell and $K^+$ into the cell; the pump maintains a low intracellular $Na^+$ (approximately 20 mmol/L) and a high intracellular $K^+$ (approximately 150 mmol/L). Thus, by maintaining a low intracellular $Na^+$ concentration, the Na-K-ATPase provides the energy for both $Cl^-$ secretion and $Na^+$ absorption.

Evidence that the $Na^+$ pump is located only on the basolateral side of the cells came from the observation that ouabain, an inhibitor of Na-K-ATPase, inhibits transport only when added to the submucosal surface; addition to the mucosal side had no effect. Studies of ouabain binding also showed localization over the basolateral cell membrane. Although the activity of the $Na^+$ pump is required for transepithelial transport, that activity dose not directly control the rate of transport. Rather, the rate is primarily controlled by the ion channels present in both cell membranes and, possibly, by the $Cl^-$ entry step at the basolateral membrane.

Potassium, which enters the cell on the $Na^+$ pump (and may also do so in the $Na^+-K^+-Cl^-$ entry step), must exit across the basolateral membrane because there is very little $K^+$ secretion in most secretory epithelia. $K^+$ accumulates in the cell above electrochemical equilibrium and thus can flow passively out of the cell through basolateral $K^+$ channels. The patch-clap technique, combined with studies of transepithelial current and isotope fluxes, revealed that $K^+$ can exit across the basolateral membrane through at least two types of $K^+$ channels, those gated by $Ca^{2+}$ and those gated by some other factor, probably cAMP.

This exit of $K^+$ across the basolateral membrane plays two important physiologic roles. First, it maintains a negative intracellular voltage, which is important for driving $Cl^-$ exit across the apical membrane. Second, it prevents cell swelling, which would otherwise result from entry of $K^+$. Thus, the activity of the basolateral $K^+$ channels contributes to the overall rate of transport.

The apical membrane of airway epithelial cells contains $Cl^-$ channels, which, when activated, provide pores through which $Cl^-$ can move passively, down a favorable electrochemical gradient into the mucosal solution. Recent work indicates that the cystic fibrosis transmembrane conductance regulator (CFTR) is the $Cl^-$ channel responsible for cAMP-mediated $Cl^-$ secretion. Addition of a hormone, such as a $\beta$-adrenergic agonist, or a toxin, such as cholera toxin, leads to an increase in cAMP, activation of cAMP-dependent protein kinase, and phosphorylation of the CFTR $Cl^-$ channel, which causes the channel to open. An increase in cell $Ca^{2+}$ can also activate different apical membrane channels. Phosphorylation by protein kinase C can either open or shut $Cl^-$ channels in the apical membrane.

Accordingly a primary objective of the present invention is to develop an effective treatment for secretory diarrhea.

Another objective of the present invention is to develop an effective treatment for secretory diarrhea that involves the electrolyte transport mechanism, which is the underlying cause of secretory diarrhea.

Another objective of the present invention is to provide a treatment for secretory diarrhea, which involves use of agents that block the CFTR chloride channel, these agents include sulfonylureas and related agents that have been called potassium channel blockers and openers; prevention of the chloride channel transfer mechanism will prevent diseases involving secretion, such as diarrhea.

Another objective of the present invention is to provide a pharmaceutically acceptable composition, especially adapted for oral dosage, which contains some of the active compounds of the present invention in a pharmaceutically acceptable oral dosage carrier.

The method and manner of accomplishing each of the above objectives, as well as others, will become apparent from the detailed description of the invention which follows hereinafter.

SUMMARY OF THE INVENTION

The disclosed invention relates to a method of treating secretory diarrhea. The method involves administering active compounds which interfere with cellular mechanism of electrolyte transport which usually accompanies secretory diarrhea. In particular, by administering the compounds which are CFTR chloride channel blockers, the chloride secretion phenomenon usually accompanying secretory diarrhea is blocked. As a result the disease is effectively treated.

DETAILED DESCRIPTION OF THE INVENTION

The cystic fibrosis transmembrane conductance regulator (CFTR) is a Cl$^-$ channel that is regulated by cAMP-dependent phosphorylation and by intracellular ATP. Intracellular ATP also regulates a class of K$^+$ channels that have a distinct pharmacology: they are inhibited by sulfonylureas and activated by a novel class of drugs called K$^+$ channel openers. In search of modulators of CFTR Cl$^-$ channels, we examined the effect of sulfonylureas and K$^+$ channel openers on CFTR Cl$^-$ currents in cells expressing recombinant CFTR.

Mutations in a single gene encoding cystic fibrosis transmembrane conductance regulator (CFTR) cause the disease cystic fibrosis (CF) (Riordan, Rommens, Kerem, Alon, Rozmahel, Grzelczak, Zielenski, Lok, Plavsic, Chou et al., 1989). Amino acid sequence analysis and comparison with other proteins suggests that CFTR consists of five domains: two membranespanning domains, each composed of six transmembrane segments; an R domain, which contains several consensus sequences for phosphorylation by cAMP-dependent protein kinase (PKA); and two nucleotide binding domains (NBDs), which are predicted to interact with ATP. Such analyses also suggest that CFTR belongs to a family of proteins that have been called the traffic ATPases (Ames, Mimura, and Shyamala, 1990) or the ABC transporters (Hyde, Emsley, Hartshorn, Mimmack, Gileadi, Pearce, Gallagher, Gill, Hubbard, and Higgins, 1990). Some members of this family hydrolyze ATP to transport substrate across cell membranes.

Recent work suggests that CFTR is a Cl$^-$ channel That conclusion is based on four observations. First, expression of recombinant CFTR in a wide variety of epithelial and nonepithelial cells generated cAMP-activated Cl$^-$ channels (Drumm, Pope, Cliff, Rommens, Marvin, Tsui, Collins, Frizzell, and Wilson, 1990; Rich, Anderson, Gregory, Cheng, Paul Jefferson, McCann, Klinger, Smith, and Welsh. 1990; Anderson, Rich, Gregory, Smith, and Welsh, 1991c; Bear, Duguay, Naismith, Kartner, Hanrahan, and Riordan, 1991; Kartner, Hanrahan, Jensen, Naismith, Sun, Ackerley, Reyes, Tsui, Romments, Bear, and Riordan, 1991). Second, the properties of cAMP-regulated Cl$^-$ channels generated by recombinant CFTR were the same as those of cAMP-regulated Cl$^-$ channels in the apical membrane of secretory epithelia, where the CF defect is located (Anderson, Sheppard, Berger, and Welsh, 1992). Third. mutation of specific basic residues within the membrane-spanning domains to acidic residues altered the channel's anion selectivity (Anderson, Gregory, Thompson, Souza, Paul, Mulligan, Smith, and Welsh, 1991). Fourth, when purified recombinant CFTR was incorporated into planar lipid bilayers it displayed regulated Cl$^-$ channel activity (Bear, Li, Kartner, Bridges, Jensen, Ramjeesingh, and Riordan, 1992).

The CFTR Cl$^-$ channel is regulated by cAMP: in experiments using the whole-cell and cell-attached configurations of the patch-clamp technique, cAMP agonists activated CFTR Cl$^-$ currents (Drumm et al., 1990; Rich et al., 1990; Anderson et al., 1991c; Bear et al., 1991; Berger, Anderson, Gregory, Thompson, Howard, Maurer, Mulligan, Smith, and Welsh, 1991; Kartner et al., 1991; Tabcharani, Chang, Riordan, and Hanrahan, 1991). This regulation occurs via phosphorylation, since addition of the catalytic subunit of cAMP-dependent protein kinase to the cytoslic surface of excised inside-out membrane patches activated CFTR Cl$^-$ channels (Berger et al., 1991; Tabcharani et al., 1991). The R domain is the site of PKA-dependent regulation because four serine residues in the R domain are phosphorylated in vivo when cellular levels of cAMP increase (Cheng, Rich, Marshall, Gregory, Welsh, and Smith, 1991). Mutation of those serines to alanines abolishes cAMP-dependent activation (Cheng et al., 1991). Moreover, expression of CFTR in which part of the R domain has been deleted produces Cl$^-$ channels that are constitutively active; that is, channel activation does not require an increase in cellular cAMP levels (Rich, Gregory, Anderson, Manavalan, Smith, and Welsh, 1991).

Nucleoside triphosphates, such as ATP, also regulate the CFTR Cl$^-$ channel: once phosphorylated by PKA, micromolar concentrations of ATP are required to maintain channel activity (Anderson, Berger, Rich, Gregory, Smith, and Welsh, 1991a). ATP activates the channel via a mechanism independent of both PKA and the R domain; regulation at the NBDs is an attractive explanation for this effect.

Intracellular ATP also regulates a class of K$^+$ channels (ATP-senssiitive K$^+$ channels; K-ATP channels) (Noma, 1983; Cook and Hales, 1984; Ashcroft and Ashcroft, 1990). the opening of K-ATP channels in pancreatic $\beta$ cells, myocytes, and some neurons is coupled to the cytoplasmic concentration of ATP. In contrast to the CFTR Cl$^-$channel where ATP activates the channel, micromolar concentrations of ATP inhibit K-ATP channels (Ashcroft and Ashcroft, 1990). Although the primary structure of K-ATP channels is presently unknown, their regulation by ATP suggests that they may share some similarity with CFTR Cl$^-$ channels.

K-ATP channels have a distinct pharmacology: they are inhibited by sulfonylureas, such as tolbutamide and glibenclamide, a group of hypoglycemia-inducing drugs used to treat diabetes mellitus (Sturgess, Ashford, Cook, and Hales, 1985). K-ATP channels are also activated by a novel class of drugs known as K$^+$ channel openers (Edwards and Weston, 1990); Standen, Quayle, Davies, Brayden, Huang, and Nelson, 1989). These agents include cromakalim, a potent smooth muscle relaxant with hypotensive and bronchodilatory activity in vivo, as well as diazoxide, an antihypertensive drug also used to treat some pancreatic carcinomas (Dunne and Petersen, 1991).

In contrast, the pharmacology of CFTR Cl$^-$ channels is less well defined. The search for modulators of CFTR Cl$^-$ channels is important in at least three respects. First, no high affinity inhibitors of CFTR Cl$^-$ channels have yet been identified; such inhibitors might be useful as agents for distinguishing CFTR Cl$^-$ channels and as probes of the mechanism of ion permeation. Second, novel pharmacological activators of CFTR Cl$^-$ channels might provide an important therapy for the defective Cl$^-$secretion across CF epithelia. Third, inhibitors of Cl$^-$ channels could be used to inhibit Cl secretion in diseases such as secretory diarrhea.

In accordance with the present invention it has been discovered that either a CFTR chloride channel blocker or a potassium channel opener, in fact, inhibits or blocks the chloride channel and therefore should effectively treat secretory diarrhea. Those CFTR chloride channel blockers that can be used most effectively are sulfonylurea compounds, and in particular tolbutamide or glibenclamide or their related analogs. Especially preferred, and the very most effective chloride channel blocker found to date, is glibenclamide and its related analogs.

For reasons not completely understood, it has been found, as demonstrated by the examples below, that potassium channel openers also function effectively as chloride channel blockers. In particular, testing to date has revealed that diazoxide and lemakalim and minoxidil sulfate all function effectively in this regard. These compounds have the structures set forth below:

SULFONYLUREAS tolbutamide

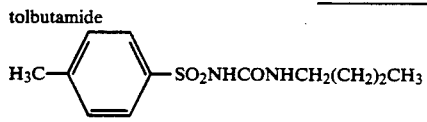

glibenclamide

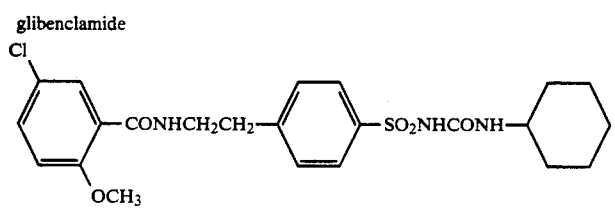

POTASSIUM CHANNEL OPENERS diazoxide  lemakalim 

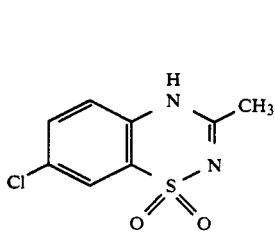

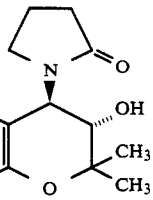

minoxidil sulphate 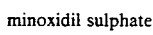

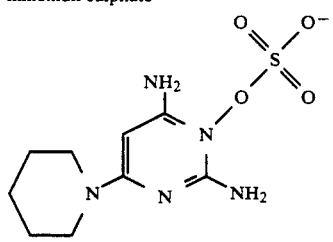

These compounds are either water soluble or easily water miscible and therefore can be effectively carried in conventional pharmaceutical carriers of a non-toxic nature, suited for oral dosage.

The dosage level can vary widely, as can the dosing frequency. Generally the dosage level should be from 1.0 microgram to 100 micrograms and the frequency be w n doses during the treatment should be from about 4 to 24 hours.

The following examples show successful uses of CFTR chloride channel blockers and potassium channel openers as inhibitors of the chloride channels and certain cell lines. In particular for these studies NIH 3T3 fibroblasts were used that had been stably infected with a retrovirus expressing either wild-type human CFTR (Gregory, Cheng, Rich, Marshall, Paul, Hehir, Ostedgaard, Klinger, Welsh, and Smith, 1990) or a CFTR mutant in NBD2 (CFTR-K1250M, in which lysine 1250 was charged to methionine) (Anderson et al., 1991a). These two stable cell lines were generated with the generous help of Dr. S. Thompson and Dr. R. C. Mulligan (Whitehead Institute, Massachusetts Institute of Technology, Cambridge, Mass.). We also transiently expressed another mutant (CFTR-K-335E, in which lysine 335 in the first transmembrane domain was changed to glutamic acid) in HeLa cells using the vaccinia virus-T7 hybrid expression system (Rich et al., 1990; Elroy-Stein, Fuerst, and Moss, 1989). CFTR, in which part of the R domain was deleted (amino acids 708-835; CFTRΔR) (Rich et al., 1991), was stably expressed in a mouse mammary cell line (C127 cells). This stable C127 cell line was generate by first inserting CFTRΔR cDNA in place of wild-type CFTR cDNA in a bovine papilloma virus (BPV)-based expression vector. The CFTRΔR plasmid was then introduced into C127 cells using calcium phosphate and transfectants were selected by neomycin resistance. This stable C127 cell line was obtained from Dr. R. J. Gregory and Dr. A. E. Smith (Genzyme Corp., Framingham, Mass.). Cells were maintained in culture as previously described (Rich et al., 1990). Patch pipettes were backfilled with an intracellular solution containing (mM): 120 N-methyl-D-glucamine, 85 aspartic acid, 3 $MgCl_2$, 1 CsEGTA (ethyleglycolbis-($\beta$-aminoethyl ether)N,N,N$^1$, N$^1$-tetraacetic acid, cesium salt; Sigma Chemical Co., St. Louis, Mo.), 1 MgATP, and 5 TES (N-Tris(hydroxymethyl)methyl-2-aminoethane sulfonic acid), and pH was adjusted to 7.3 with HCl, yielding a Cl⁻ concentration of 43 mM. By replacing K⁺ in the intracellular solution with the impermeant cation N-methyl-D-glucamine, K⁺-selective currents were inhibited. The free $Ca^{2+}$ concentration of the intracellular solution was $<10^{-8}$ M.

Cells were washed in $Ca^{2+}$-and $Mg^{2+}$-free phosphate-buffered saline and briefly treated with 0.25% (wt/vol) tryspin to detach them from the plastic Petri dishes on which they were grown. This treatment did not affect the properties of CFTR Cl⁻ currents. Small aliquots of cells were placed in a chamber (volume=0.5 cm³) mounted on the stage of an inverted microscope and bathed in an extracellular solution containing (mM): 140 NaCl, 1.2 MgSO₄, 1.2 CaCl₂, 10 dextrose, and 10 TES (pH 7.3 with NaOH). Test solutions were gently perfused into the bath and removed by a vacuum pump. All solutions were filtered through 0.45-μm filters (Millipore Corp., Bedford, Mass.) and experiments were conducted at 34°-36° C. using a temperature controlled microscope stage (Brook Industries, Lake Villa, Ill.).

Patch pipettes were fabricated from thin-walled borosilicate glass capillary tubing (Rochester Scientific Co., Rochester, N.Y.) using a two-stage vertical pipette puller (model 750; David Kopf Instruments, Tujunga, Calif.) and coated with Sylgard (Dow Corning Corp., Midland, Mich.). Pipette tips were polished using a microforge. Patch pipettes had resistances of 2–4 MΩ when filled with intracellular solution.

Whole-cell membrane currents were recorded according to the method of Hamill, Marty, Neher, Sakmann, and Sigworth (1981) using a List EPC-7 amplifier (List-Medical, Germany). Seals of 10–40 CΩ were routinely obtained. Cells were clamped at a holding potential of 0 mV and membrane currents were measured during depolarizing and hyperpolarizing voltage steps.

The established sign convention was used throughout. That is, ionic currents produced by positive charge moving from intra- to extracellular solutions (anions moving in the opposite direction) and shown as positive currents. The bath electrode consisted of an Ag-AgCl pellet connected to the bathing solution via an agar bridge filled with 1 M KCl.

A microcomputer (IBM AT compatible) and the pClamp software package (Axon Instruments, Inc., Foster City, Calif.) were used for pulse generation, data acquisition, and analysis. Voltage-pulse protocols were applied to the stimulus input of the List EPC-7 amplifier after digital-to-analog conversion using a TL-1 DMA interface (Axon Instruments, Inc.). The signal from the amplifier, which was filtered at 0.5-2.5 kHz using a variable 8-pole Bessel filter (Frequency Devices Inc., Haverhill, Mass.) was simultaneously viewed on a storage oscilloscope and acquired using pClamp software.

Adenosine trisphosphate magnesium salt (MgATT), 8-4-chlorophenylthio)-adenosine 3':5'-cyclic monophosphate sodium salt (CPT-cAMP), forskolin, 3-isobutyl-1-methylxanthine (IBMX), and TES were purchased from Sigma Chemical Co.

Stock solutions of the sulfonylureas and diazoxide were prepared in dimethyl sulfoxide and BRL 38227 in 70% (vol/vol) ethanol; minoxidil sulfate was prepared in acetone according to the manufacturer's instructions. Drugs were diluted in extracellular solution to achieve final concentrations at the time of use. The vehicle solutions did not affect CFTR Cl⁻ currents (n=4 in each case).

Cells expressing CFTR exhibited little or no CL⁻-selective current under baseline conditions. Addition of cAMP agonists (10 μM forskolin and 100 μM IBMX, or 500 μM CPT-cAMP, a membrane-permeant cAMP analogue) activated large Cl⁻ selective currents. The current-voltage (I-V) relationship of the cAMPregulated Cl⁻ current was linear and the currents exhibited no evidence of voltage-dependent activation or inactivation. In preliminary experiments, CFTR Cl⁻ current levels were stable over 3–5 min after activation.

The effect of the sulfonylurea drugs tolbutamide and glibenclamide was determined by adding the were activated by cAMP agonists. 500 μM tolbutamide inhibited CFTR Cl⁻ currents. Inhibition of CFTR Cl⁻ currents showed little voltage dependence.

Glibenclamide inhibits K-ATP channels more potently than tolbutamide.

Inhibition by both sulfonylureas developed slowly; 3 min after adding 1 mM tolbutamide or 100 μM glibenclamide, CFTR Cl⁻ currents were inhibited by >90%.

A second slower phase of current decay was also observed. This probably represents current "rundown", a phenomenon that has been previously documented for CFTR Cl⁻ channels (Berger et al., 1991). CFTR Cl⁻ currents partially recovered from tolbutamide treatment with washes lasting >10 min. However, glibenclamide inhibition was irreversible even upon prolonged washing.

Sulfonylurea inhibition was concentration-dependent.

The potassium channel openers diazoxide, lemakalim and minoxidil sulfate were also tested to determine whether potassium channel openers could stimulate CFTR channels in NIH 3T3 fibroblasts.

Diazoxide (100–1,000 μM), lemakalim (250 μM), and minoxidil sulfate (10–500 μM) had no effect on baseline currents (n=3 in each case). However, the subsequent activation of CFTR Cl⁻ currents by cAMP-mediated agonists was consistently attenuated in the presence of K⁺ channel openers when compared with that normally observed upon cAMP stimulation. Because of this result, we examined the effect of K⁺ channel openers on CFTR Cl⁻ currents that had previously been activated by cAMP agonists.

After CFTR Cl⁻ currents were activated by cAMP agonists we added either diazoxide, lemakalim, or minoxidil sulfate to the bathing solution. In each case, Cl⁻ current was inhibited. Inhibition showed little v was observed with the sulfonylureas, inhibition by the K⁺ channel openers developed slowly; 3 min after adding 1 mM diazoxide, 250 μM diazoxide, 250 μM lemakalim, or 100 μM minoxidil sulfate CFTR Cl⁻ currents were inhibited by >70%. A second slower phase of current decay was also observed which probably represents current "rundown". Inhibition was poorly reversible 5-min time intervals; longer washes were not tested.

Inhibition by K⁺ channel openers was concentration dependent. Minoxidil sulfate was more potent than lemakalim, which was more potent than diazoxide.

Sulfonylureas are highly lipid soluble, suggesting that they may permeate the plasma membrane to exert their effect. This idea is supported by the finding that sulfonylureas are equally effective in inhibiting K-ATP channels when applied to the intra- or extracellular membrane surface (Belles et al., 1987, Gillis et al., 1989). In addition, increasing extracellular pH slows the onset of tolbutamide inhibition of K-ATP channels, suggesting that the undisassociated form of the drug is the active moiety (Zünkler, Trube, and Panten, 1989). The slow onset of sulfonylurea inhibition of CFTR Cl− currents is consistent with the idea that the drugs permeate the cell membrane to exert their effect. The initial work here was done to fin agents that would activate CFTR. The thinking was that the discovery of novel pharmacological activators of CFTR chloride channels might provide a new therapeutic strategy for treating cystic fibrosis patients. Although agents that activated CFTR were not found, the finding that CFTR is inhibited by sulfonylureas and potassium channel openers suggests an interaction and raises the possibility that related agents may ultimately prove to be valuable activators of CFTR. Moreover, the CFTR channel blockers and the potassium channel openers, and particularly the potency of glibenclamide inhibition of the CFTR channel, suggests that it is of value in the design of synthesis drugs for secretory diseases, such as secretory diarrhea as discussed herein.

What is claimed is:

1. A method of treating secretory diarrhea, said method comprising;
    administering to a patient showing symptoms of secretory diarrhea, a small but treatment effective amount of a compound selected from the group consisting of CFTR chloride channel blockers and potassium channel openers.

2. The method of claim 1 wherein the compound is a CFTR chloride channel blocker.

3. The method of claim 2 wherein the CFTR chloride channel blocker is a sulfonylurea.

4. The method of claim 3 wherein said sulfonylurea compound is selected from the group consisting of tolbutamide, and glibenclamide and related analogs.

5. The method of claim 4 wherein the glibenclamide.

6. The method of claim 1 wherein the compound is a potassium channel opener.

7. The method of claim 6 wherein the potassium channel opener is selected form the group consisting of diazoxide, lemakalim and minoxidil sulfate.

* * * * *

UNITED STATES PATENT AND TRADEMARK OFFICE
CERTIFICATE OF CORRECTION

PATENT NO.  : 5,234,922  
DATED       : August 10, 1993  
INVENTOR(S) : Welsh et al.

It is certified that error appears in the above-identified patent and that said Letters Patent is hereby corrected as shown below:

Column 1,  
Beginning on line 6, please insert  
-- FEDERAL FUNDING NOTICE  
This work was supported in part by NIH Grants HL29851. --

Signed and Sealed this

Second Day of September, 2003

JAMES E. ROGAN  
*Director of the United States Patent and Trademark Office*